United States Patent [19]

Burd

[11] Patent Number: 4,911,807
[45] Date of Patent: Mar. 27, 1990

[54] FRACTIONATION AND SAMPLE LOADING BY CASSETTE IN CAPILLARY ELECTROPHORESIS

[75] Inventor: Samuel Burd, Oakland, Calif.
[73] Assignee: Bio-Rad Laboratories, Inc., Hercules, Calif.
[21] Appl. No.: 403,527
[22] Filed: Sep. 5, 1989
[51] Int. Cl.⁴ .............................................. C25B 7/00
[52] U.S. Cl. .............................. 204/180.1; 204/183.3; 204/299 R
[58] Field of Search .............. 204/180.1, 183.3, 299 R

[56] References Cited

U.S. PATENT DOCUMENTS

| 3,320,148 | 5/1967 | Skeggs | 204/180.1 |
| 3,616,453 | 10/1971 | Philpot | 204/182.8 |
| 3,867,271 | 2/1975 | Hoefer | 204/299 R |
| 4,048,049 | 9/1977 | Hoefer | 204/299 R |

Primary Examiner—John F. Niebling
Assistant Examiner—David G. Ryser
Attorney, Agent, or Firm—Townsend and Townsend

[57] ABSTRACT

Short capillary segments are introduced in succession into the current path of a capillary electrophoresis system, either at the downstream end of the separation capillary for purposes of collecting the eluting species in fractions, or at the upstream end for purposes of sequential sample loading. The segments are preferably contained in mobile cassettes whose motion is governed by either continuous or stepper motors at a controlled rate depending on which position the cassette occupies in the solute migration path.

22 Claims, 1 Drawing Sheet

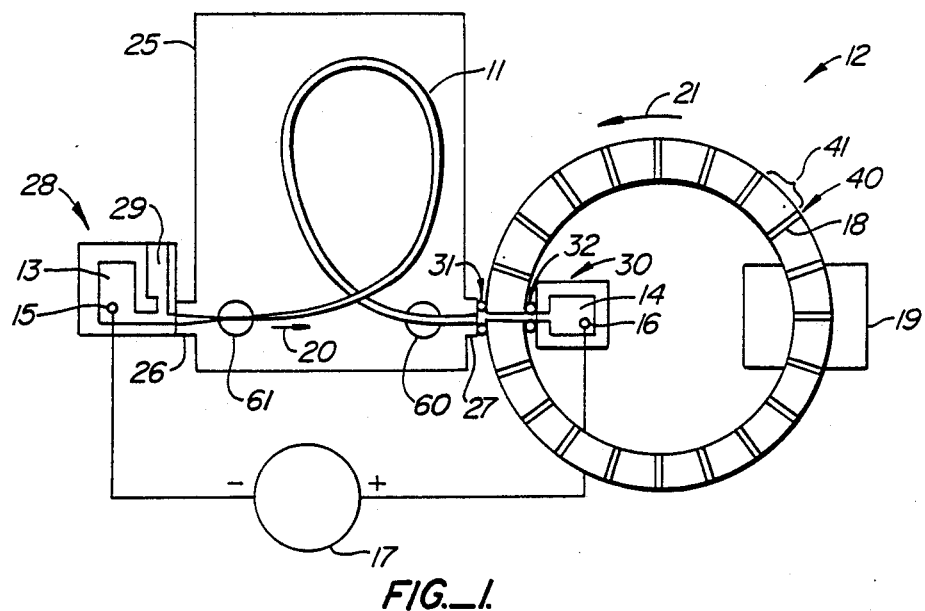
FIG._1.
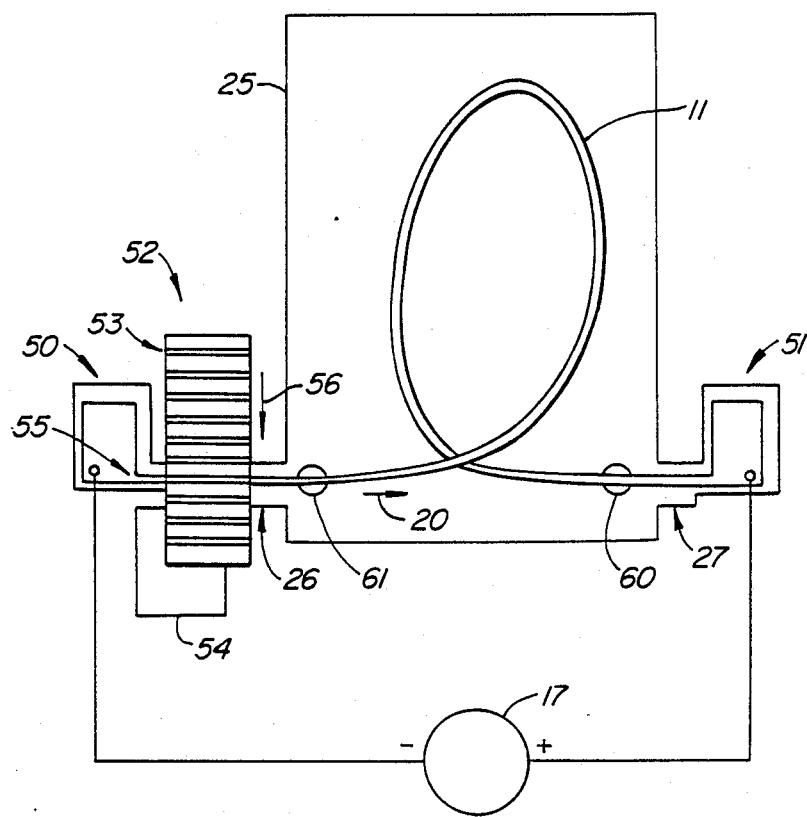
FIG._2.

ical separations at high speed. In addition, the small diameter of the capillary is well adapted to the separation of extremely small samples, making the system particularly useful with samples which are obtainable only in small amounts. Capillary electrophoresis also lends itself to the use of a buffer solution as the separation medium, avoiding the use of complex media such as gel or paper yet avoiding band broadening. Still further, capillaries by virtue of their flexibility can be used to provide a relatively long separation path permitting the separation of a large number of components in a single sample, including those which are closely related. Further still, capillary tubes are well suited to on-line detection of the separated species by the use of a light beam passing through the capillary at a point toward the exit end, the emerging beam directed to a detector.

FRACTIONATION AND SAMPLE LOADING BY CASSETTE IN CAPILLARY ELECTROPHORESIS

This invention lies in the field of capillary electrophoresis, and particularly in the area of methods and apparatus for the handling of samples entering and eluents leaving a capillary electrophoresis column.

BACKGROUND AND SUMMARY OF THE INVENTION

Capillary electrophoresis is known for the advantages it offers in certain applications. One advantage is that it permits use of high voltages by virtue of the ease of cooling a capillary tube. High voltages are particularly useful in performing electrophoretic separations at high speed. In addition, the small diameter of the capillary is well adapted to the separation of extremely small samples, making the system particularly useful with samples which are obtainable only in small amounts. Capillary electrophoresis also lends itself to the use of a buffer solution as the separation medium, avoiding the use of complex media such as gel or paper yet avoiding band broadening. Still further, capillaries by virtue of their flexibility can be used to provide a relatively long separation path permitting the separation of a large number of components in a single sample, including those which are closely related. Further still, capillary tubes are well suited to on-line detection of the separated species by the use of a light beam passing through the capillary at a point toward the exit end, the emerging beam directed to a detector.

Disclosed herein are capillary electrophoresis systems with further useful features, broadening their range of application and further facilitating their use. In particular, this invention provides the repeated replacement of a segment along the solute migration path. In accordance with this innovation, a series of volumes of liquid medium may be placed successively in the path of the electric current, each one subsequently removed for replacement by a fresh volume. The process may be repeated in an extended sequence, or as few times as once. The invention lends itself to automation, as well as a high degree of precision in terms of volumes, migration path lengths and contact time intervals.

The invention has two primary embodiments, one in which the interchangeable segments are positioned at the downstream end of the larger, main body of the capillary, and the other in which the segments are placed at the upstream end. In the former, the segments are used to separate the species eluting from the larger capillary into separate receptacles, from which they may be separately recovered, detected, treated, or otherwise processed. In the latter, the segments may be used to load a series of samples onto the larger capillary in sequence at controlled time intervals. In further embodiments of the invention, the two features are combined, thereby achieving both repetitive and sequential sample loading at one end of the capillary and the separation and isolation of eluant fractions at the other.

In all embodiments, the interchangeable path segments are in the form of capillary passages of relatively short length compared to the length of the capillary through which the main portion, if not the entirety, of the electrophoretic separation takes place. The short interchangeable passages will be referred to herein for convenience as "capillary segments," whereas the longer length of capillary in which the major portion of the separation takes place and which remains in the current path at all times will be referred to as the "separation capillary," This invention extends to all systems in which the capillary segments and separation capillary move with respect to each other, thereby bringing the capillary segments one at a time into fluid communication (and electrical communication) with the separation capillary. In preferred and most convenient embodiments, the separation capillary will be mounted or supported in a stationary manner and the capillary segments will be mobile, their motion controlled in accordance with their intended function. The separation capillary will most conveniently be retained and supported in a housing or support, such as for example an enclosed cartridge, such that the capillary end which communicates with the capillary segments is readily accessible to them and can be readily aligned and placed in fluid contact with the segments in succession. The capillary segments are conveniently contained in a common block or structural member which can be drawn across the exposed opening of the separation capillary. In certain embodiments, a fluid-tight seal is maintained at the juncture between the capillary segments and the separation capillary, and in further embodiments, this seal is one which will prevent leakage when the system is placed under a positive pressure such as the pressures encountered during pressurized sample loading.

Further features and advantages of the invention will be apparent from the description which follows.

BRIEF DESCRIPTION OF THE DRAWINGS

FIG. 1 is a representation of an electrophoretic system employing a cassette of short capillary passages positioned at the eluting or exit end of a capillary separation column, illustrating one embodiment of the present invention.

FIG. 2 is a representation of a second embodiment of the invention, in which a cassette of short capillary passages is positioned at the introduction or upstream end of the capillary column.

DETAILED DESCRIPTION OF THE INVENTION AND PREFERRED EMBODIMENTS

The embodiment depicted in FIG. 1 illustrates the incorporation of the capillary segments in a cassette for the collection of fractions eluting from the separation capillary. Basic elements of the system include a separation capillary 11, the fraction collector cassette 12, buffer reservoirs 13, 14, a cathode 15, anode 16, and power source 17. The capillary segments 18 are capillary-sized panels extending through the fraction collector cassette 12, each channel open at both ends. A motor 19 drives the cassette 12, bringing the capillary segments 18 one at a time into alignment with the separation capillary 11 and the buffer reservoir 14. Each capillary segment aligned in this manner provides a continuous fluid path between the separation capillary 11 and the buffer reservoir 14 permitting the passage of an electric current and consequently the passage of solutes by electrophoretic migration. The direction of solute migration during electrophoresis is indicated by an arrow 20. Similarly, the direction of rotation of the fraction collector cassette 12 is indicated by the arrow 21.

The present invention functions by the relative motion of the cassette and the separation capillary with respect to each other. Thus, either of the two may be stationary while the other is mobile, or both may be mobile, i.e. any arrangement which causes the capillary segments to enter the current path one at a time in succession. In most applications, the most convenient arrangement will be one in which the separation capillary is stationary and the capillary segments are contained in a mobile cassette, particularly one with a controlled motion, i.e., at a controlled or programmed rate. The cassette may also assume a variety of physical forms and shapes, with the type of translational motion selected accordingly. In the embodiment shown in FIG. 1, the cassette 12 is circular in shape, with the capillary segments arranged radially and distributed around the cassette circumference. The cassette motion is accordingly a rotational motion in the direction of the arrow 21 around an axis passing through the center of the circle perpendicular to the plane of the figure.

The system shown in the drawing includes a combination of individual parts, mated for simple and easy assembly, used in association with other parts such as supports or housings, alignment devices, detection equipment, and sample injection and column flushing features, as well as other features and accessories, all of which are known in the art and may be supplied by conventional technology. The separation capillary 11 in this embodiment is contained in a cartridge 25 which serves to protect the capillary as well as to provide for on-line detection capability, cooling by heat exchange with a circulating fluid if desired, and simple and easy attachment to the other parts with fluid-tight seals. The cartridge is an enclosed housing with the separation capillary looped inside a sufficient number of times to provide the desired length. The two ends of the separation capillary are fused into ports 26, 27 in the cartridge walls, permitting full access to the capillary interior for fluid entry and exit and current flow.

At the entry side of the capillary is a buffer reservoir 13 containing the cathode 15. This reservoir 13 is contained in a block 28 which may contain additional features to facilitate sample loading and other manipulations useful in preparing the system for a run. A sample reservoir 29 is included in the block for sample introduction. Appropriate valves, ports, and other features and attachments not shown in the drawing will be included for various functions such as overflow, flushing, and evacuation. The juncture between the block 28 and the cartridge inlet port 26 will be one which provides a flow path between the various reservoirs in the cartridge and the separation capillary 11 while maintaining a fluid-tight seal, preferably one which can withstand elevated pressures such as those encountered during pressurized sample loading techniques.

At the opposite end of the separation capillary 11 is the anode 16 and its associated buffer solution 14, contained in an outlet block 30. The outlet block 30 will typically contain additional features, not shown in the drawing, similar to those in the inlet block 28, all within the realm of conventional technology. The cassette 12 is positioned to pass between the outlet port 27 on the separation capillary cartridge and the outlet block 30, with the capillary segments adjoining the two whenever they come into alignment. If fluid-tight seals are used, they must nevertheless permit motion of the cassette 12 past the cartridge outlet port 27 and the outlet block 30, both of which are stationary, while still maintaining the seals on both sides. This may be achieved by conventional means, such as appropriately sized O-rings 31, 32 as shown, or some other sealing mechanism.

In the embodiment shown in FIG. 1, it will be noted that the capillary segments 18 are spaced apart at intervals around the cassette 12. The external openings 40 of adjacent capillary segments are separated by portions of solid external wall 41. In the arrangement shown, these intervening wall portions close off the separation capillary 11 and interrupt the current path whenever the capillary segments 18 are not in alignment between the separation capillary 11 and the outlet buffer reservoir 14. With the current path interrupted in this manner, the electrophoretic migration of solute species within the separation column 20 as well as all other portions of the apparatus is momentarily suspended while the cassette rotates further and brings the next capillary segment into position. Thus, no components of the sample are lost and the entire elution profile will be distributed among the various capillary segments in the cassette.

Turning now to FIG. 2, the present invention is shown as a means of achieving multiple periodic sample introduction into a capillary electrophoresis system. As in FIG. 1, the separation capillary 11 is contained in a cartridge 25, with the electrical system set up to produce solute migration in the direction of the arrow 20. An inlet block 50 and an outlet block 51, similar to those in the FIG. 1 embodiment, are included. The outlet block 51 however is adapted to mate directly with the outlet port 27 of the cartridge 25. A cassette 52 with multiple capillary segments 53 is positioned between the inlet block 50 and the inlet port 26 of the cartridge 25. A stepper motor 54 governs both the position and the motion of the cassette 52, bringing the capillary segments 53 one at a time into alignment with the fluid passage 55 leading into the inlet block reservoir and the inlet port 26 of the cartridge.

The capillary segments 53 in this embodiment are each filled with samples to be separated electrophoretically in the separation column 11, and the stepper motor 54 permits these samples to be inserted in the current path in periodic sequence. As in FIG. 1, the external walls of the cassette 52 include portions between the openings of each of the capillary segments on both sides, and these intervening portions, when passing over the capillary openings, interrupt the electric current path, momentarily suspending solute migration. In order to achieve continuous electrophoresis of an entire sample prior to introduction of a new sample into the separation capillary, the cassette may be held motionless with one of the capillary segments in the current path both during sample introduction and for a specified time thereafter. Alternatively, a new sample may be introduced while one which has been previously been introduced is still passing through the separation capillary 11.

In the embodiment shown in FIG. 2, the cassette is rectangular in shape, and the capillary segments 53 are placed in a parallel arrangement. Mobility of the cassette occurs in the direction shown by the arrow 56.

A variety of additional features may be incorporated into either of these systems. On-line detection, for example, may be achieved through a window 60 in the separation capillary cartridge 25, positioned toward the downstream end of the capillary 11, adjacent to a small segment of the capillary. Mated windows on both sides of the cartridge (only one being shown in the drawings) permit the directing of a light beam, such as that from an ultraviolet light source, through the capillary, with a detector positioned to receive the emerging light beam.

The window on the entry side will generally contain a lens to focus the light beam on the capillary.

A similar window 61 at the upstream side of the capillary may be included to monitor sample injection, with a similar arrangement of light source, lens and detector. Signals from either or both of the windows may be used for a variety of purposes. For example, the window at the inlet end 61 may be used to coordinate the motor 54 driving the sample cassette 52 for sample introduction. Alternatively, the same signal could be used to start the motion of a fraction collector cassette such as that shown in FIG. 1 (cassette 12). Still further, the downstream window may be used to generate signals governing the motion of either a sample loading cassette 52 as in FIG. 2 or a fraction collector cassette 12 as in FIG. 1. In controlling the fraction collector cassette 12, the associated motor 19 driving the cassette may be governed by the signal emerging from the downstream-side window 60 to result in placement of a single solute in each of the capillary segments. Other possibilities may be apparent to those skilled in the art.

Further options include arrangements whereby a cooling fluid is circulated through the interior of the cartridge 25 around the separation capillary 11, as well as structures and components for various different types of sample loading, including bulk flow loading by pressure differential.

The materials and dimensions of the various components used in accordance with the present invention are not critical and may vary widely. In most applications, it will be most convenient to use capillary segments having the same diameter as the separation capillary, a common range being approximately 25 to approximately 50 microns in diameter. Capillary segments will generally be of relatively short length, a typical length being on the order of 1 to 4 centimeters, while the separation capillary is on the order of 10 to 100 centimeters. A cassette in accordance with the invention may contain any number of capillaries. In most cases, a typical number will generally be between 5 and 50. The spacing of the capillaries in the cassette will primarily be a matter of manufacturing and handling convenience. In general, for a continuous-motion cassette, the distance between adjacent capillaries will generally be at least about twice the diameter of a single capillary, and the length of time that any one capillary is in the current path may range from 10 to 30 seconds.

The foregoing is offered primarily for purposes of illustration. It will be readily apparent to those skilled in the art that further variations may be introduced without departing from the spirit and scope of the invention.

What is claimed is:

1. Apparatus for capillary electrophoresis involving the insertion of a series of discrete volumes of separation media in sequence in the current path, said apparatus comprising:
   a first structural member with a capillary passage therethrough defined as a separation capillary;
   a second structural member with a series of additional capillary passages therethrough defined as capillary segments;
   moving means for moving said first and second structural members with respect to each other to place said capillary segments one at a time in communication with said separation capillary: and
   power supply means for imposing an electric potential across the combined lengths of said separation capillary and the capillary segment in communication therewith.

2. Apparatus in accordance with claim 1 in which said first structural member is stationary and said moving means moves said second structural member across said first structural member.

3. Apparatus in accordance with claim 1 in which capillary segments terminate in openings spaced at intervals along a common external wall of said second structural member, and said moving means draws said external wall across an open end of said separation capillary in such a manner that said openings are brought one at a time into alignment with said open end and the portions of said external wall between said openings close said open end between such times that said openings and said open end are in alignment.

4. Apparatus in accordance with claim 3 in which said first and second structural members are arranged such that said portions of said external wall between said openings close said open end between said times in fluid-tight manner.

5. Apparatus in accordance with claim 3 in which said first and second structural members are arranged such that said portions of said external wall between said openings close said open end between said times in a manner sufficient to provide a fluid-tight seal with a positive pressure differential between the interior of said separation capillary and the environment surrounding said apparatus.

6. Apparatus in accordance with claim 1 in which said power supply means comprises first and second buffer reservoirs each containing an electrode, said first and second buffer reservoirs arranged with said first and second structural members in between said first and second buffer reservoirs to form a continuous fluid path through the combined lengths of said separation capillary and any capillary segment in communication therewith.

7. Apparatus in accordance with claim 6 in which said first structural member is stationary and said moving means moves said second structural member across said first structural member, and in which said power supply means imposes a constant electric potential between said electrodes as said second structural member is moved across said first structural member.

8. Apparatus in accordance with claim 1 in which said power supply means defines a solute migration direction along the combined lengths of said separation capillary and the capillary segment in communication therewith, and said first structural member is arranged upstream of said second structural member with respect to said direction.

9. Apparatus in accordance with claim 1 in which said power supply means defines a solute migration direction along the combined lengths of said separation capillary and the capillary segment in communication therewith, and said first structural member is arranged downstream of said second structural member with respect to said direction.

10. Apparatus in accordance with claim 1 in which said first structural member is stationary and said moving means moves said second structural member across said first structural member at a continuous steady rate.

11. Apparatus in accordance with claim 1 in which said first structural member is stationary and said moving means moves said second structural member across said first structural member in stepwise manner to hold each of said capillary segments in communication with said separation capillary for a time interval of preselected duration.

12. Apparatus in accordance with claim 1 in which said second structural member is a circular cassette and said capillary segments are arranged radially therein, and said moving means rotates said circular cassette.

13. Apparatus in accordance with claim 1 in which said second structural member is a rectangular block with said capillary segments running parallel therethrough, and said moving means draws said rectangular block linearly past said first structural member.

14. A method of performing electrophoresis along a solute migration path in a capillary electrophoresis system whereby a plurality of discrete bodies of separation medium are inserted interchangeably into said solute migration path, said method comprising:
 (a) filling a capillary passage with separation medium, said capillary passage extending through a first structural member and defined as a separation capillary;
 (b) placing said discrete bodies of separation medium in individual discrete capillary passages, defined as capillary segments, extending through a second structural member;
 (c) moving said first and second structural members with respect to each other to place said capillary segments one at a time in alignment with said separation capillary; and
 (d) upon alignment of each said capillary segment with said separation capillary, imposing an electrical potential across the combined lengths of said separation capillary and the capillary segment aligned therewith.

15. A method in accordance with claim 14 in which said capillary segments terminate in openings spaced at intervals along a common external wall of said second structural member, and step (c) comprises drawing said external wall across an open end of said separation capillary thereby bringing said openings one at a time into alignment with said open end while maintaining continuous contact between said first and second structural members such that the portions of said external wall between said openings seal off said open end between such times that said openings and said open end are in alignment.

16. A method in accordance with claim 14 in which said first structural member is stationary, step (c) comprises moving said second structural member past said first structural member, and step (d) comprises maintaining a constant electric potential between first and second electrodes in first and second buffer reservoirs, respectively, while said first and second structural members are moving with respect to each other, said first and second buffer reservoirs being arranged with respect to said first and second structural members to produce electric current through said separation capillary only when in alignment with one of said capillary segments and only through the capillary segment in alignment therewith.

17. A method in accordance with claim 14 in which said first structural member is stationary, step (c) comprises moving said second structural member past said first structural member at a continuous steady rate.

18. A method in accordance with claim 14 in which said first structural member is stationary, step (c) comprises moving said second structural member past said first structural member in stepwise manner to hold each of said capillary segments in communication with said separation capillary for a time interval of preselected duration.

19. A method in accordance with claim 14 in which said second structural member is a circular cassette with said capillary segments arranged radially therein, and step (c) comprises rotating said circular cassette thereby drawing said capillary segments past said separation capillary.

20. A method in accordance with claim 14 in which said second structural member is a rectangular block with said capillary segments running parallel therethrough, and step (c) comprises drawing said rectangular block linearly past said first structural member.

21. A method of performing electrophoresis in a capillary electrophoresis system while collecting eluant therefrom in discrete fractions, said method comprising:
 (a) loading a capillary having first and second ends with sample at said first end, said capillary being filled with electrophoretic separation medium and defined as a separation capillary;
 (b) drawing a member with capillary passages therethrough defined as capillary segments across said second end of said separation capillary thereby placing said capillary segments one at a time in alignment with said separation capillary, said capillary segments being filled with electrophoretic separation medium;
 (c) simultaneously with step (b), imposing an electric potential across the combined lengths of said separation capillary and the capillary segment in alignment therewith to cause electrophoretic migration of said sample through said separation capillary and to fractionate eluant therefrom into said capillary segments.

22. A method of performing electrophoresis on a series of samples in succession, said method comprising:
 (a) placing said samples in capillary passages contained in a member, said capillary passages defined as capillary segments;
 (b) drawing said member across a further capillary passage filled with electrophoretic separation medium, said further capillary passage defined as a separation capillary, thereby placing said capillary segments one at a time in alignment with said separation capillary; and
 (c) simultaneously with step (b), imposing an electric potential across the combined lengths of said separation capillary and the capillary segment in alignment therewith to cause electrophoretic introduction of the sample contained in said capillary segment into said separation capillary and to cause electrophoretic migration of the sample so introduced through said separation capillary.

* * * * *